United States Patent

Sakamoto et al.

Patent Number: 5,480,858
Date of Patent: Jan. 2, 1996

[54] CYCLOHEXANEDIONE DERIVATIVES

[75] Inventors: Masashi Sakamoto; Mitsuru Shibata; Ichiro Nasuno; Kazuyoshi Koike, all of Sodegaura, Japan

[73] Assignee: Idemitsu Kosan Co., Ltd., Tokyo, Japan

[21] Appl. No.: 373,218

[22] PCT Filed: Aug. 6, 1993

[86] PCT No.: PCT/JP93/01107

§ 371 Date: Jan. 13, 1995

§ 102(e) Date: Jan. 13, 1995

[87] PCT Pub. No.: WO94/04524

PCT Pub. Date: Mar. 3, 1994

[30] Foreign Application Priority Data

Aug. 18, 1992 [JP] Japan .................... 4-219477

[51] Int. Cl.$^6$ ............ A01N 43/18; A01N 43/16; C07D 335/06
[52] U.S. Cl. ............ 504/288; 504/292; 549/23; 549/28; 549/401; 549/403
[58] Field of Search ............ 549/23, 28, 401, 549/403; 514/432, 456, 457; 504/288, 292

[56] References Cited

U.S. PATENT DOCUMENTS

| | | | |
|---|---|---|---|
| 4,741,755 | 5/1988 | Knudsen et al. | 549/28 |
| 4,895,868 | 1/1990 | Chandraratna | 514/432 |
| 5,006,150 | 4/1991 | Lee et al. | 549/28 |
| 5,074,903 | 12/1991 | Jahn et al. | 549/28 |
| 5,114,461 | 5/1992 | Geach et al. | 549/28 |
| 5,132,434 | 7/1992 | Watanabe et al. | 549/28 |
| 5,424,320 | 6/1995 | Fortin et al. | 549/283 |

FOREIGN PATENT DOCUMENTS 0079637  5/1983  European Pat. Off. .

*Primary Examiner*—Glennon H. Hollrah
*Assistant Examiner*—Deborah Lambkin
*Attorney, Agent, or Firm*—Frishauf, Holtz, Goodman, Langer & Chick

[57] ABSTRACT

Cyclohexanedione derivatives of the formula (I),

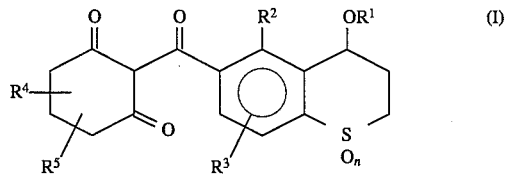

wherein $R^1$ is a $C_1$–$C_6$ alkyl group, $R^2$ is a $C_1$–$C_4$ alkyl group, each of $R^3$, $R^4$ and $R^5$ is independently hydrogen or a $C_1$–$C_4$ alkyl group, and n is an integer of 0 to 2, or salts thereof exhibit high selectivity for corn, wheat and barley, and can control gramineous weeds and broad-leaved weeds at low dosages.

27 Claims, No Drawings

CYCLOHEXANEDIONE DERIVATIVES

TECHNICAL FIELD

The present invention relates to a cyclohexanedione derivative. More specifically it relates to a novel cyclohexanedione derivative, a process for the production thereof and a herbicide containing the cyclohexanedione derivative as an active ingredient.

TECHNICAL BACKGROUND

During a growing period of corn, etc., a triazine-containing herbicide such as atrazine and acetoanilide-containing herbicides such as alachlor and metolachlor have been conventionally used. However, atrazine shows low efficacy to gramineous weeds, and alachlor and metolachlor show low efficacy to broad-leaved weeds. It is therefore difficult at present to control gramineous weeds and broad-leaved weeds together using a single herbicide. Further, the use of these chemicals in combination fails to give any sufficient effect. Moreover, the above herbicides are undesirable in view of an environmental problem due to their high dosage requirement.

On the other hand, it is known that specific benzoylcyclohexanedione derivatives have herbicidal activity (see JP-B-1-30818, JP-A-61-155347, JP-A-1-143851, JP-A-3-120202, EP 135,191, EP 186,118A, EP 186,119A, U.S. Pat. No. 4,954,165, GB 2,215,333A, EP 336,898A, U.S. Pat. Nos. 4,937,386, 4,780,127, 5,092,919 and PCT International Publication 90/05712). Typical examples of the above benzoylcyclo-hexanedione derivatives are as follows.

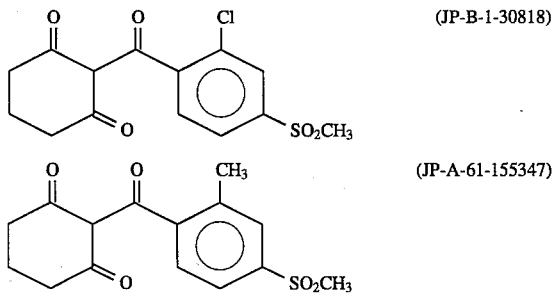

Further, JP-A-64-6256 discloses cyclohexanedione derivatives having a fused dicyclic group containing heteroatoms.

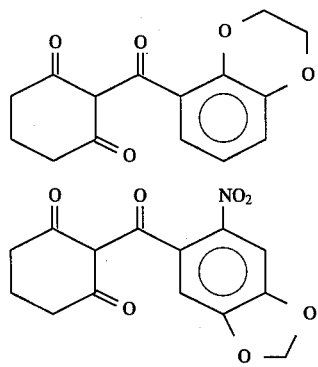

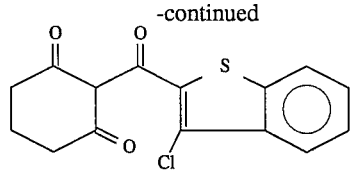

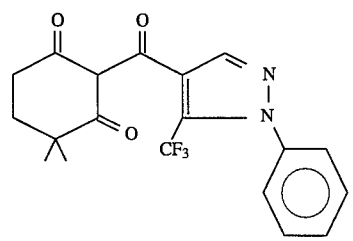

However, cyclohexanedione derivatives having a thiochroman ring such as compounds of the present invention are not known yet.

Further, the cyclohexanedione derivatives that have been already disclosed are insufficient in practical use, particularly poor in herbicidal activity to gramineous weeds such as barnyardgrass and green foxtail.

It is therefore a first object of the present invention to provide a novel cyclohexanedione derivative which exhibits high selectivity for corn, wheat and barley and can control both gramineous weeds and broad-leaved weeds at low dosage.

It is a second object of the present invention to provide a process for the production of the above novel cyclohexanedione derivative.

Further, it is a third object of the present invention to provide a herbicide containing the above novel cyclohexanedione derivative as an active ingredient.

DISCLOSURE OF THE INVENTION

The novel cyclohexanedione derivative of the present invention, which achieves the first object of the present invention, is a compound of the formula (I).

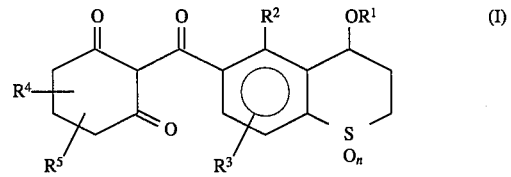

In the formula (I), $R^1$ is a $C_1$–$C_6$ alkyl group such as methyl, ethyl, propyl, butyl, pentyl or hexyl. The propyl, butyl, pentyl and hexyl may be linear or branched. $R^1$ is preferably a $C_1$–$C_4$ alkyl group, more preferably methyl, ethyl or isopropyl.

$R^2$ is a $C_1$–$C_4$ alkyl group such as methyl, ethyl, propyl or butyl. The propyl and butyl may be linear or branched. $R^2$ is preferably methyl.

Each of $R^3$, $R^4$ and $R^5$ is independently hydrogen or a $C_1$–$C_4$ alkyl. The $C_1$–$C_4$ alkyl group includes those described regarding the above $R^2$. Each of $R^3$, $R^4$ and $R^5$ is preferably hydrogen or methyl. The site where $R^3$ is substituted is preferably the 8-position on a thiochroman ring. Further, both $R^4$ and $R^5$ are preferably substituted on the same carbon atom of a cyclohexane-1,3-dione ring, and the site where each of $R^4$ and $R^5$ is preferably the 4-position.

The suffix "n" indicates the number of oxygen atom(s) bonded to a sulfur atom, and n is an integer of 0 to 2. That is, when n=0, sulfide is represented. When n=1, sulfoxide is represented. When n=2, sulfone is represented. The sulfone form (n=2) is preferred.

Specific examples of the cyclohexanedione derivative of the formula (I) are preferably as shown in Table (A).

TABLE (A)

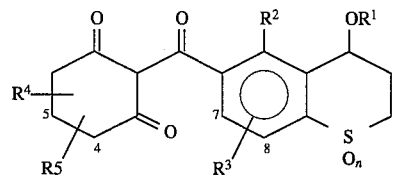

| Compound No. | $R^1$ | $R^2$ | $R^3$ | $R^4$ | $R^5$ | n |
|---|---|---|---|---|---|---|
| 1 | $CH_3$ | $CH_3$ | H | H | H | 0 |
| 2 | $CH_3$ | $CH_3$ | H | H | H | 1 |
| 3 | $CH_3$ | $CH_3$ | H | H | H | 2 |
| 4 | $C_2H_5$ | $CH_3$ | H | H | H | 0 |
| 5 | $C_2H_5$ | $CH_3$ | H | H | H | 1 |
| 6 | $C_2H_5$ | $CH_3$ | H | H | H | 2 |
| 7 | $n-C_3H_7$ | $CH_3$ | H | H | H | 0 |
| 8 | $n-C_3H_7$ | $CH_3$ | H | H | H | 2 |
| 9 | $i-C_3H_7$ | $CH_3$ | H | H | H | 0 |
| 10 | $i-C_3H_7$ | $CH_3$ | H | H | H | 2 |
| 11 | $n-C_4H_9$ | $CH_3$ | H | H | H | 2 |
| 12 | $i-C_4H_9$ | $CH_3$ | H | H | H | 2 |
| 13 | $sec-C_4H_9$ | $CH_3$ | H | H | H | 2 |
| 14 | $n-C_6H_{13}$ | $CH_3$ | H | H | H | 2 |
| 15 | $CH_3$ | $CH_3$ | $7-CH_3$ | H | H | 0 |
| 16 | $CH_3$ | $CH_3$ | $7-CH_3$ | H | H | 2 |
| 17 | $CH_3$ | $CH_3$ | $8-CH_3$ | H | H | 0 |
| 18 | $CH_3$ | $CH_3$ | $8-CH_3$ | H | H | 2 |
| 19 | $C_2H_5$ | $CH_3$ | $7-CH_3$ | H | H | 2 |
| 20 | $C_2H_5$ | $CH_3$ | $8-CH_3$ | H | H | 2 |
| 21 | $n-C_3H_7$ | $CH_3$ | $7-CH_3$ | H | H | 2 |
| 22 | $n-C_3H_7$ | $CH_3$ | $8-CH_3$ | H | H | 2 |
| 23 | $i-C_3H_7$ | $CH_3$ | $7-CH_3$ | H | H | 2 |
| 24 | $i-C_3H_7$ | $CH_3$ | $8-CH_3$ | H | H | 2 |
| 25 | $n-C_4H_9$ | $CH_3$ | $8-CH_3$ | H | H | 2 |
| 26 | $n-C_6H_{13}$ | $CH_3$ | $8-CH_3$ | H | H | 2 |
| 27 | $CH_3$ | $C_2H_5$ | H | H | H | 2 |
| 28 | $CH_3$ | $C_2H_5$ | $8-CH_3$ | H | H | 2 |
| 29 | $CH_3$ | $C_2H_5$ | $8-C_2H_5$ | H | H | 2 |
| 30 | $CH_3$ | $i-C_3H_7$ | H | H | H | 2 |
| 31 | $CH_3$ | $i-C_3H_7$ | $8-CH_3$ | H | H | 2 |
| 32 | $CH_3$ | $i-C_3H_7$ | $8-C_2H_5$ | H | H | 2 |
| 33 | $CH_3$ | $i-C_3H_7$ | $8-i-C_3H_7$ | H | H | 2 |
| 34 | $CH_3$ | $n-C_4H_9$ | H | H | H | 2 |
| 35 | $CH_3$ | $n-C_4H_9$ | $8-n-C_4H_9$ | H | H | 2 |
| 36 | $C_2H_5$ | $C_2H_5$ | $8-C_2H_5$ | H | H | 2 |
| 37 | $n-C_3H_7$ | $n-C_3H_7$ | $8-n-C_3H_7$ | H | H | 2 |
| 38 | $n-C_4H_9$ | $n-C_4H_9$ | $8-n-C_4H_9$ | H | H | 2 |
| 39 | $C_2H_5$ | $CH_3$ | $8-CH_3$ | $5-CH_3$ | $5-CH_3$ | 2 |
| 40 | $C_2H_5$ | $CH_3$ | $8-CH_3$ | $4-CH_3$ | $4-CH_3$ | 2 |
| 41 | $CH_3$ | $CH_3$ | $8-CH_3$ | $4-CH_3$ | $4-CH_3$ | 2 |
| 42 | $i-C_3H_7$ | $CH_3$ | $8-CH_3$ | $4-CH_3$ | $4-CH_3$ | 2 |
| 43 | $CH_3$ | $CH_3$ | H | $4-CH_3$ | $4-CH_3$ | 2 |
| 44 | $C_2H_5$ | $CH_3$ | H | $4-CH_3$ | $4-CH_3$ | 2 |
| 45 | $C_2H_5$ | $CH_3$ | $8-CH_3$ | H | H | 1 |

The cyclohexanedione derivative of the formula (I) has an asymmetric carbon atom, and include two isomers. The cyclohexanedione derivative of the present invention includes any one of these isomers and a mixture of these isomers.

Further, the cyclohexanedione derivative of the Formula (I) can have the following tautomer structures. The cyclohexanedione derivative of the present invention includes any one of compounds having these structures and a mixture of at least two of the compounds having these structures.

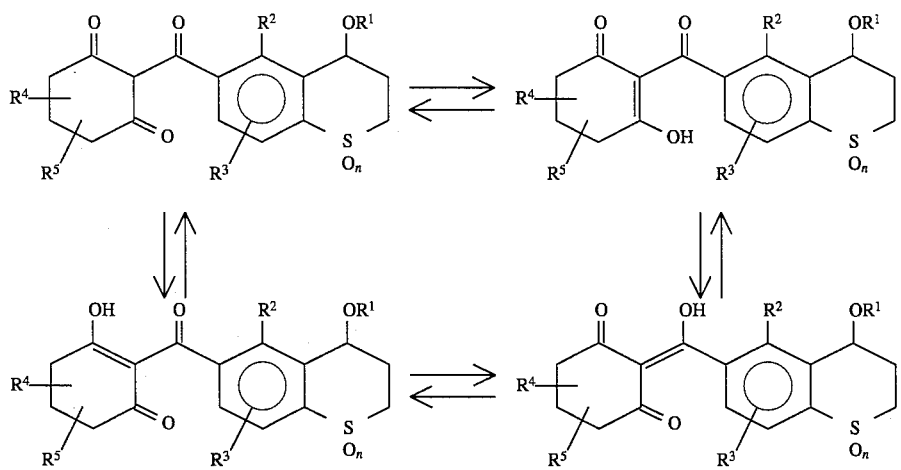

Further, the cyclohexanedione derivative of the Formula (I) is an acidic substance, and can be easily converted to a salt by treating it with a base. The cyclohexanedione derivative of the present invention also includes this salt.

The above base is selected from known bases and not specially limited. Examples of the base include organic bases such as amines and anilines and inorganic bases such as ammonia, sodium salts and potassium salts.

Examples of the amines include alkylamines such as alkylamine, dialkylamine and trialkylamine. The alkyl group of the alkylamines is generally a $C_1$–$C_4$ alkyl. Examples of the anilines include non-N-substituted anilines and alkylanilines such as alkylaniline and dialkylaniline. The alkyl group of the alkylanilines is generally a $C_1$–$C_4$ alkyl group.

Examples of the sodium salts include sodium hydroxide and sodium carbonate. Examples of the potassium salts include potassium hydroxide and potassium carbonate.

The process for producing the cyclohexanedione derivative of the formula (I), provided by the present invention, will be described hereinafter.

That is, the process for producing the cyclohexanedione derivative of the formula (I) comprises reacting a compound of the formula (II),

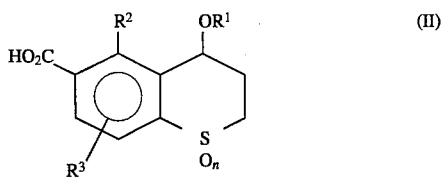

wherein $R^1$, $R^2$, $R^3$ and n are as defined in the formula (I), with a halogenating agent to form a compound of the formula (III),

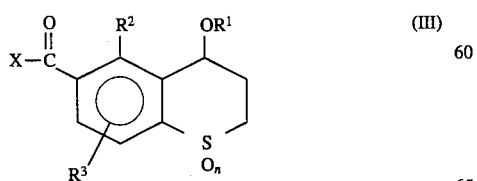

wherein $R^1$, $R^2$, $R^3$ and n are as defined in the formula (I) and X is a halogen atom, reacting the above compound (III) with a compound of the formula (IV),

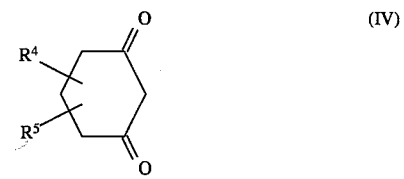

wherein $R^4$ and $R^5$ are as defined in the formula (I), to form a compound of the Formula (V),

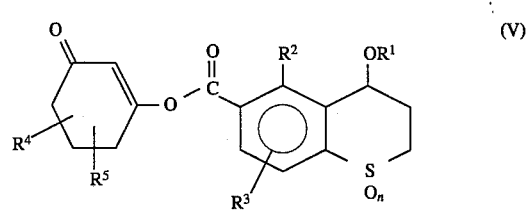

wherein $R^1$, $R^2$, $R^3$, $R^4$, $R^5$ and n are as defined in the above formula (I), and subjecting the above compound to a rearrangement reaction to form the cyclohexanedione derivative of the above,

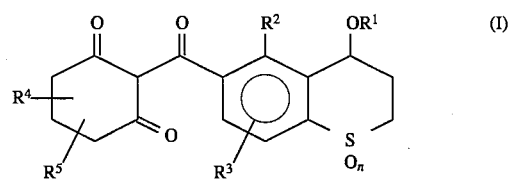

wherein $R^1$, $R^2$, $R^3$, $R^4$, $R^5$ and n are as defined in the above.

For facile understanding of the above process of the present invention, the reaction scheme thereof will be illustrated below.

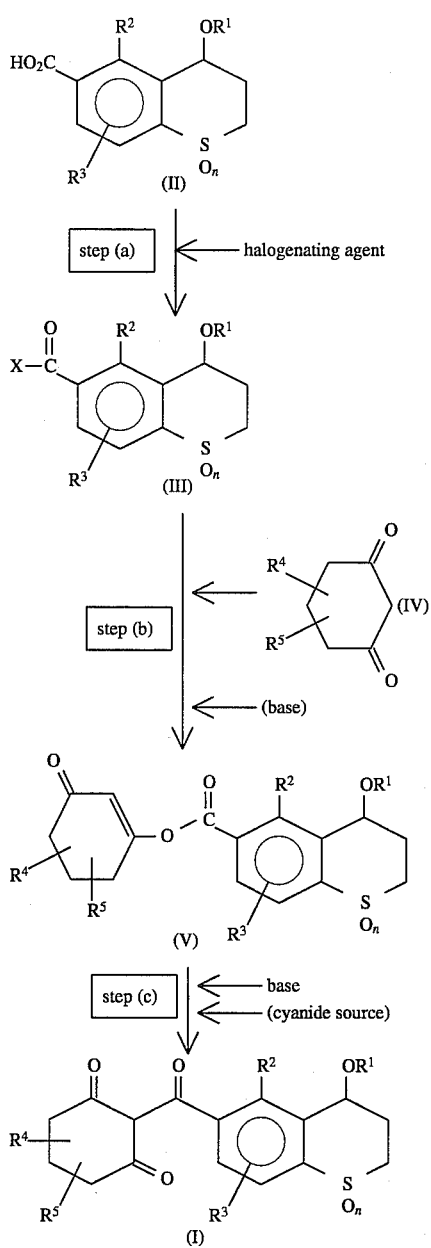

In step (a), the compound of the formula (II) is allowed to react with a halogenating agent (such as thionyl chloride or phosphorus oxychloride) to obtain the compound of the formula (III). In step (a), the amount of the halogenating agent is preferably equimolar to, or larger than, the amount of the compound (II). This reaction may be carried out in a solvent (methylene chloride, chloroform, and the like) or without a solvent. An excess amount of thionyl chloride that is a halogenating agent may be used as a solvent. The reaction temperature is not specially limited, while the reaction temperature is preferably from 0° C. to the boiling point of the solvent, particularly preferably 60° C. or around 60° C.

In step (b), the compound of the formula (III) obtained in step (a) is allowed to react with the compound of the formula (IV) to obtain the compound of the formula (V). In step (b), the amount of the compound of the formula (IV) per mole of the compound of the formula (III) is preferably 1 to 3 mol, and the reaction is preferably carried out in a solvent, inert to the reaction, such as dioxane, acetonitrile, benzene, toluene, chloroform, methylene chloride or 1,2-dichloroethane. The reaction may be carried out in a biphase solvent such as water-benzene, water-toluene or water-chloroform. The reaction smoothly proceeds in a co-presence of an equimolar amount or a larger amount of a base such as sodium hydroxide, potassium hydroxide, sodium carbonate, potassium carbonate, triethylamine or pyridine. The reaction temperature is preferably 0° to 60° C., more preferably 0° C. to room temperature.

In step (c), the compound of the formula (V) obtained in step (b) is subjected to a rearrangement reaction to obtain the cyclohexanedione derivative of the formula (I). The reaction in this step (c) is preferably carried out in a solvent inert to the reaction, such as methylene chloride, 1,2-dichloroethane, toluene, acetonitrile, N,N-dimethylformamide or ethyl acetate. Acetonitrile is particularly preferred. In step (c), a proper base (such as sodium carbonate, potassium carbonate, triethylamine or pyridine) is used, and the amount of the base is 1 to 4 times, preferably 1 to 2 times, as large as the equivalent of the compound of the formula (V). In this step (c), the reaction smoothly proceeds in a catalytic co-presence of a so-called "cyanide source", a compound which can generate hydrogen cyanide or cyanide anion in the reaction system. Examples of the cyanide source include metal cyanides such as sodium cyanide and potassium cyanide, and cyanohydrin compounds of lower alkyl ($C_1$–$C_4$) ketones such as acetone cyanohydrin and methyl isopropyl ketone cyanohydrin. When a metal cyanide is used, a phase transfer catalyst such as crown ether may be added in the reaction system. The amount of the cyanide source per equivalent of the compound of the formula (V) is 0.01 to 0.5 equivalent, preferably 0.05 to 0.2 equivalent. The reaction temperature is preferably 0° to 80° C., more preferably 20° to 40° C.

The above compound of the formula (II) used as a starting material for the production of the cyclohexanedione derivative of the formula (I) is a useful as an intermediate compound for synthesizing the herbicide, and can be synthesized by various methods. For example, it can be synthesized through steps (i), (ii), (iii) and (iv) as illustrated in the following reaction schemes (A) and Scheme (A)

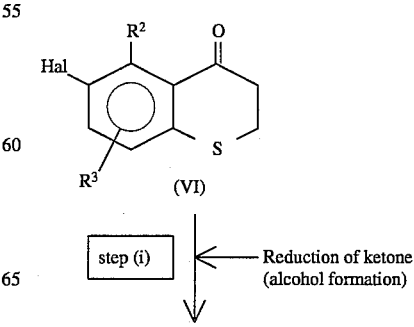

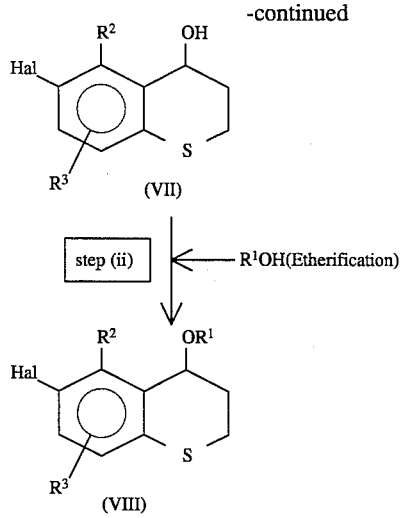

-continued

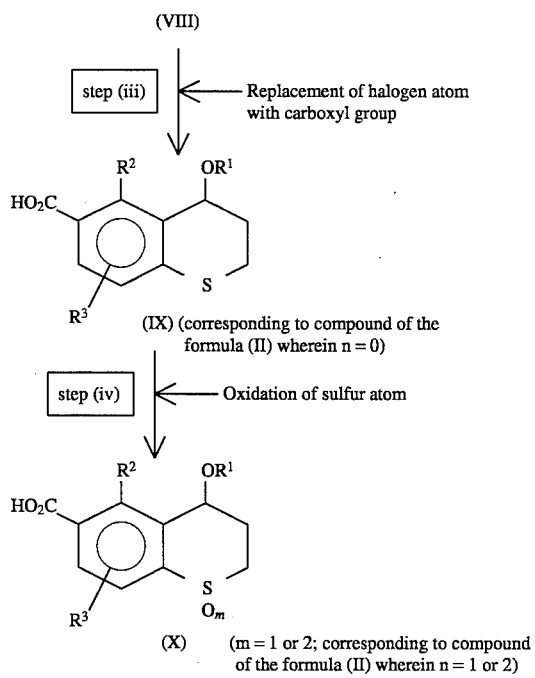

Scheme (B)

The steps (i), (ii), (iii) and (iv) will be explained hereinafter.

In step (i), a ketone of the formula (VI) is reduced to form an alcohol of the Formula (VII). The reaction temperature is generally −20° to 50° C. The reducing agent includes various agents, and sodium borohydride is among them. The ketone of the formula (VI) as a starting material can be produced by various methods, for example, by the methods described in PCT International Publication WO88/06155 and JP-A-58-198483.

In step (ii), the alcohol of the formula (VII) and an alcohol of the formula of $R^1OH$ are condensed by dehydration to form the ether of the formula (VIII). In this reaction system, there can be used aromatic hydrocarbons such as benzene, toluene and xylene and halogenated hydrocarbons such as 1,2-dichloroethane and carbon tetrachloride. When the alcohol $R^1OH$ is used in an excess amount, it also works as a solvent. The reaction proceeds smoothly in the presence of a catalyst, and the catalyst is selected from acid catalysts such as sulfuric acid, aromatic sulfonic acid, sulfonyl halide, boron trifluoride and aluminum chloride. The reaction temperature is generally 60° C. to the boiling point of the solvent used, but when the boiling point is not less than 100° C., preferably the reaction temperature is less than 100° C.

In step (iii), the compound of the formula (VIII) and magnesium are allowed to react to form a Grignard reagent, and carbon dioxide is allowed to react with this Grignard reagent to form the carboxylic acid of the formula (IX) (a compound of the formula (II) wherein n=0). The reaction temperature is generally 0° to 50° C. The solvent used therefor is preferably diethyl ether or tetrahydrofuran.

In step (iv), the sulfur atom in the compound of the formula (IX) is oxidized to form the compound of the formula (X). The compound of the formula (X) corresponds to a compound of the formula (II) wherein n is 1 (sulfoxide) or 2 (sulfone). The reaction temperature is generally room temperature to 100° C. The oxidizing agent is selected from various agents, and hydrogen peroxide is particularly preferred. The solvent used therefor is selected from various solvents, and acetic acid is particularly preferred. For forming the sulfoxide, the reaction is carried out in the presence of 1 equivalent of the oxidizing agent at room temperature. For forming the sulfone, the reaction is carried out in the presence of at least 2 equivalent of the oxidizing agent at 50° to 100° C.

The so-obtained compound of the formula (II), i.e., the compound of the formula (IX) or (X), can be preferably used as a starting material for the production of the cyclohexanedione derivative of the formula (I) provided by the present invention.

The herbicide of the present invention contains, as an active ingredient, the novel cyclohexanedione derivative of the formula (I) and/or its salt, provided by the present invention. These compounds can be used in any form of a wettable powder, an emulsion, a dust and granules by mixing the cyclohexanedione derivative and/or its salt with a liquid carrier such as a solvent or a solid carrier such as a fine mineral powder. For imparting these compounds with emulsifiability, dispersibility and wettability in producing the above preparations, a surfactant can be added.

When the herbicide of the present invention is used in the form of a wettable powder, a composition is prepared by mixing 10 to 55% by weight of the cyclohexanedione derivative of the present invention and/or the salt thereof, 40 to 88% by weight of a solid carrier and 2 to 5% by weight of a surfactant, and the resultant composition is be used. When it is used in the form of an emulsion, generally, it can be prepared by mixing 20 to 50% by weight of the cyclohexanedione derivative of the present invention and/or the salt thereof, 35 to 75% by weight of a solvent and 5 to 15% by weight of a surfactant.

On the other hand, when the herbicide of the present invention is used in the form of dust, generally, the dust can be prepared by mixing 1 to 15% by weight of the cyclohexanedione derivative of the present invention and/or the salt thereof, 80 to 97% by weight of a solid carrier and 2 to 5% by weight of a surfactant. Further, when it is used in the form of granules, the granules can be prepared by mixing 1 to 15% by weight of the cyclohexanedione derivative of the present invention and/or the salt thereof, 80 to 97% by weight of a solid carrier and 2 to 5% by weight of a surfactant. This solid carrier is selected from fine mineral powders, and examples of these fine mineral powders include oxides such as diatomaceous earth, slaked lime, phosphates such as apatite, sulfates such as gypsum, and silicates such as talc, pyrophyllite, clay, kaolin, bentonire, acid clay, white carbon. powdered quartz and a silica powder.

The above solvent is selected from organic solvents, and specific examples of the organic solvents include aromatic hydrocarbons such as benzene, toluene and xylene, chlorinated hydrocarbons such as o-chlorotoluene, trichloromethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, dimethyl ether and methyl ethyl ether, esters such as isopropyl acetate, benzyl acetate and methyl fumarate, amides such as dimethylformamide, and mixtures of these.

Further, the above surfactant is selected from anionic surfactants, nonionic surfactants, cationic surfactants and amphoteric surfactants (amino acid and betaine).

The herbicide of the present invention may contain other herbicidally active component as required in combination with the cyclohexanedione derivative of the formula (I) and/or the salt thereof as an active ingredient. This "other" herbicidally active component includes known herbicides such as phenoxy, diphenylether, triazine, urea, carbamate, thiolcarbamate, acetanilide, pyrazole, phosphoric acid, sulfonylurea and oxadiazon herbicides. This "other" herbicide is properly selected from these herbicides.

Further, the herbicide of the present invention may be used in combination with an insecticide, a fungicide, a plant growth regulator and a fertilizer as required.

The present invention will be explained further in detail with reference to Examples, while the present invention shall not be limited thereto.

Preparation Example 1

1-a)

A 100 ml eggplant-shaped flask was charged with 7.3 g (0.024 mol) of 4-ethoxy-5,8-dimethylthiochroman-6-carboxylic acid-1,1-dioxide and 20 ml of thionyl chloride, and the mixture was allowed to react at 60° C. for 30 minutes. After the reaction, an excess of thionyl chloride was distilled off under reduced pressure, and then 40 ml of methylene chloride was added to the residual oil to form a solution. Then, 3.1 g (0.028 mol) of cyclohexane-1,3-dione was added, and while the solution was cooled at 0° to 10° C., 3.1 g (0.031 mol) of triethylamine was added dropwise. The mixture was stirred at room temperature for 6 hours, and about 200 ml of methylene chloride was added. The resultant solution was consecutively washed with a 2% hydrochloric acid aqueous solution, water and a saturated sodium hydrogencarbonate aqueous solution and then dried over anhydrous sodium sulfate, and methylene chloride was distilled off under reduced pressure. The residual oil was purified through a silica gel column to give 8.6 g of 4-ethoxy-5,8-dimethyl-8-(3-oxycyclohexenyl)oxycarbonylthiochroman- 1,1-dioxide (yield 90%).

1-b)

A 100 ml eggplant-shaped flask was charged with 8.6 g (0.022 mol) of 4-ethoxy-5,8-dimethyl-6-(3 -oxycyclohexenyl)oxycarbonylthiochroman-1,1-dioxide, 40 ml of acetonitrile and 4.0 g (0.040 mol) of triethylamine, and while the mixture was stirred at room temperature, 0.1 g (0.0012 mol) of acetone cyanohydrin was added dropwise. The mixture was stirred at room temperature for 2 hours, and then acetonitrile was distilled off under reduced pressure. The residue was dispersed in diethyl ether and a 3% sodium carbonate aqueous solution to form two separate phases. The aqueous layer was collected and acidified (pH 2-5) with a 5% hydrochloric acid, and then precipitate was extracted with ethyl acetate and dried over anhydrous sodium sulfate. Ethyl acetate was distilled off under reduced pressure to give 5.5 g of an intended product, 4-ethoxy-5,8-dimethyl-8-(1,3-dioxocyclohexan-2-yl)carbonyl-thiochroman-1,1-dioxide (yield 64%). The yield based on the 4-ethoxy-5,8 -dimethylthiochroman-6-carboxylic acid-1,1-dioxide was 58%. Table (C) shows the analytical data of the so-obtained compound.

Preparation Examples 2–8

The following compounds as intended products were obtained in the same manner as in Preparation Example 1 except that the 4-ethoxy-5,8-dimethylthiochroman-6-carboxylic acid-1,1-dioxide was replaced with starting materials shown in Table (B). Table (B) shows the structural formulae, outputs and yields of the intended products. Table (C) shows the analytical data.

Intended products obtained in Preparation Examples 2–8

Preparation Example 2
4-Ethoxy-5-methyl-6-(1,3-dioxocyclohexan-2 -yl)carbonylthiochroman-1,1-dioxide Preparation Example 3
4-n-Propyloxy-5-methyl-6-(1,3-dioxocyclohexan-2 -yl)carbonyl thiochroman-1,1-dioxide Preparation Example 4
4-Methoxy-5-methyl-6-(1,3-dioxocyclohexan-2 -yl)carbonylthiochroman-1,1-dioxide Preparation Example 5
4-i-Propyloxy-5-methyl-6-(1,3-dioxocyclohexan-2 -yl)carbonylthiochroman-1,1-dioxide Preparation Example 6
4-Methoxy-5,8-dimethyl-6-(1,3-dioxocyclohexan-2 -yl)carbonylthiochroman-1,1-dioxide Preparation Example 7
4-i-Propyloxy-5,8-dimethyl-6-(1,3-dioxocyclohexan-2-yl)carbonylthiochroman-1,1-dioxide Preparation Example 8
4-Ethoxy-5,8-dimethyl-6-(1,3-dioxocyclohexan-2 -yl)carbonylthiochroman-1-oxide Preparation Example 9

9.2 Grams of 4-ethoxy-5,8-dimethyl-6-(5,5 -dimethyl-1,3-dioxocyclohexan-2-yl)carbonylthiochroman-1,1-dioxide was obtained in the same manner as in Preparation Example 1 except that the cyclohexan-1,3-dione was replaced with 5,5-dimethylcyclohexan-1,3-dione (yield 89%). Table (B) shows the structural formula of the starting material and the structural formula, output and yield of the products. Table (C) shows the analytical data of the product.

Preparation Examples 10–14

The following intended products were obtained in the same manner as in Example 1 except that the cyclohexane-1,3-dione was replaced with 4,4-dimethylcyclohexane-1,3-dione and optionally that the 4-ethoxy-5,8-dimethylthiochroman-6-carboxylic acid-1,1-dioxide was replaced with a starting material shown in Table (B). Table (B) shows the structural formulae, outputs and yields of the intended products, and Table (C) shows the analytical data thereof.

Intended products obtained in Examples 10–14

Preparation Example 10
4-Ethoxy-5,8-dimethyl-6-(4,4-dimethyl-1,3 -dioxocyclohexan-2-yl)carbonylthiochroman-1,1 -dioxide Preparation Example 11
4-Methoxy-5,8-dimethyl-6-(4,4-dimethyl-1,3 -dioxocyclohexan-2-yl)carbonylthiochroman-1,1-dioxide Preparation Example 12

4-i-Propyloxy-5,8-dimethyl-6-(4,4-dimethyl-1,3-dioxocyclohexan-2-yl)carbonylthiochroman-1,1-dioxide Preparation Example 13

4-Methoxy-5-methyl-6-(4,4-dimethyl-1,3-dioxocyclohexan-2-yl)carbonylthiochroman-1,1-dioxide Preparation Example 14

4-Ethoxy-5-methyl-6-(4,4-dimethyl-1,3-dioxocyclohexan-2-yl)carbonylthiochroman-1,1-dioxide

TABLE (B)

| Prep. Ex. No. | Starting material | Structural formula | Compound No. in Table (A) | Output (g) | Yield (%) |
|---|---|---|---|---|---|
| 1 | | | 20 | 5.5 | 58 |
| 2 | | | 6 | 5.8 | 61 |
| 3 | | | 8 | 6.5 | 68 |
| 4 | | | 3 | 6.2 | 70 |
| 5 | | | 10 | — | 57 |
| 6 | | | 18 | — | 80 |
| 7 | | | 24 | — | 87 |

TABLE (B)-continued

| Prep. Ex. No. | Starting material | Structural formula | Compound No. in Table (A) | Output (g) | Yield (%) |
|---|---|---|---|---|---|
| 8 | | | 45 | — | 54 |
| 9 | | | 39 | — | 89 |
| 10 | | | 40 | — | 98 |
| 11 | | | 41 | — | 83 |
| 12 | | | 42 | — | 84 |
| 13 | | | 43 | — | 79 |
| 14 | | | 44 | — | 80 |

TABLE (C)

| Preparation Example No. | Infrared absorption spectrum *1 (cm⁻¹) | Proton nuclear magnetic resonance spectrum (ppm) | Melting point (°C.) |
|---|---|---|---|
| 1 | 1675 (C = O)<br>2920, 2970, 3000 (C—H)<br>3300~3450 (O—H) | 1.26 (3H, t), 2.0~2.9 (8H, m)<br>2.21 (3H, s), 2.71 (3H, s)<br>3.1~4.0 (4H, m), 4.55~4.61 (H, m)<br>6.94 (H, s) | *2<br>189.7<br>~190.7 |
| 2 | 1680 (C = O)<br>2900, 2950, 2980 (C—H)<br>3200~3450 (O—H) | *3<br>1.20 (3H, t), 2.0~3.1 (8H, m)<br>2.28 (3H, s), 3.2~4.0 (4H, m)<br>4.75~4.82 (H, m), 7.30 (H, d)<br>7.33~7.95 (H, m), 7.68 (H, d) | Glass-like substance |
| 3 | 1670 (C = O)<br>2890, 2940, 2970 (C—H)<br>3300~3500 (O—H) | 0.92 (3H, t), 1.61 (2H, m)<br>1.9~3.1 (8H, m), 2.28 (3H, s)<br>3.1~3.9 (4H, m), 4.73~4.80 (H, m)<br>7.30 (H, d), 7.70 (H, d)<br>7.82~8.00 (H, m) | *3<br>- ditto - |
| 4 | 1680 (C = O)<br>2830, 2950 (C—H)<br>3300~3450 (O-H) | 2.0~3.0 (8H, m), 2.27 (3H, s)<br>3.0~3.9 (2H, m), 3.45 (3H, s)<br>4.48~4.56 (H, m), 7.19 (H, d)<br>7.77~8.04 (H, m), 7.80 (H, d) | *2<br>- ditto - |
| 5 | 1680 (C = O)<br>2950, 2990 (C—H)<br>3200~3500 (O—H) | 1.23 (6H, dd), 2.0~3.1 (8H, m)<br>2.33 (3H, s) 3.2~3.9 (2H, m)<br>4.01 (H, m), 4.96~5.03 (H, m)<br>7.29 (H, d), 7.69 (H, d) | *3<br>Glass-like substance |
| 6 | 1685 (C = O)<br>2830, 2910, 2950 (C—H)<br>3300~3500 (O—H) | 1.9~2.9 (8H, m), 2.21 (3H, s)<br>2.71 (3H, s ) 3.1~4.0 (2H, m)<br>3.43 (3H, s ) 4.45~4.52 (H, m)<br>6.95 (H, s) | *2<br>210.0<br>~213.7 |
| 7 | 1690 (C = O)<br>2920, 2960, 3000 (C—H)<br>3300~3500 (O—H) | 1.24 (6H, dd), 1.9~2.9 (8H, m)<br>2.26 (3H, s) 2.71 (3H, s)<br>3.1~3.3 (H, m), 3.7~4.1 (2H, m)<br>4.77~4.84 (H, m), 6.94 (H, s) | *2<br>68.0<br>~69.3 |
| 8 | 1680 (C = O)<br>2900, 2940, 2980 (C—H)<br>3300~3450 (O—H) | 1.22 (3H, t), 1.9~2.9 (8H, m)<br>2.21 (3H, s), 2.67 (3H, s)<br>3.1~3.9 (4H, m)<br>4.52~4.61 (H, m), 6.97 (H, s) | *2<br>Glass-like substance |
| 9 | 1680 (C = O)<br>2950, 2970 (C—H)<br>3200~3500 (O—H) | 1.12 (6H, s), 1.23 (3H, t), 2.20 (3H, s)<br>2.31 (2H, s), 2.4~2.9 (2H, m)<br>2.65 (2H, s) 2.70 (3H, s)<br>3.1~4.0 (4H, m), 4.52~4.60 (H, m)<br>6.93 (H, s ) | *2<br>156.2<br>~162.6 |
| 10 | 1680 (C = O)<br>2880, 2940, 2980 (C—H)<br>3200~3450 (O—H) | 1.12 (3H, s), 1.23 (3H, t), 1.39 (3H, s)<br>1.80~1.96 (2H, m), 2.20 (3H, s)<br>2.4~2.9 (4H, m), 2.70 (3H, s)<br>3.0~4.0 (4H, m), 4.53~4.60 (H, m)<br>6.90 (H, s) | *2<br>211.2<br>~216.5 |
| 11 | 1680 (C = O)<br>2960, 2990 (C—H)<br>3300~3500 (O—H) | 1.12 (3H, s), 1.39 (3H, s)<br>1.80~2.05 (2H, m)<br>2.20 (3H, s), 2.4~2.9 (4H, m)<br>2.71 (3H, s ), 3.1~4.0 (2H, m)<br>3.43 (3H, s), 4.45~4.51 (H, m)<br>6.91 (H, s) | *2<br>120.0<br>~121.6 |
| 12 | 1680 (C = O)<br>2870, 2940, 2970 (C—H)<br>3300~3500 (O—H) | 1.13 (3H, s), 1.24 (6H, dd)<br>1.39 (3H, s), 1.80~2.05 (2H, m)<br>2.24 (3H, s), 2.4~2.9 (4H, m)<br>3.1~4.0 (3H, m), 4.75~4.83 (H, m)<br>6.90 (H, s) | *2<br>217.8<br>~219.6 |
| 13 | 1680 (C = O)<br>2830, 2880, 2940, 2970 (C—H)<br>3200~3550 (O—H) | 1.12 (3H, s), 1.37 (3H, s)<br>1.85~1.95 (2H, m), 2.25 (3H, s)<br>2.4~2.9 (4H, m), 3.08~3.90 (2H, m)<br>3.45 (3H, s), 4.48~4.55 (H, m)<br>7.17 (H, d), 7.80 (H, d) | *2<br>Glass-like substance |
| 14 | 1675 (C = O)<br>2880, 2930, 2970 (C—H)<br>3300~3450 (O—H) | 1.11 (3H, s), 1.24 (3H, t )<br>1.39 (3H, s), 1.81~1.95 (2H, m)<br>2.26 (3H, s), 2.4~2.9 (4H, m) | *2<br>- ditto - |

TABLE (C)-continued

| Preparation Example No. | Infrared absorption spectrum *1 (cm⁻¹) | Proton nuclear magnetic resonance spectrum (ppm) | Melting point (°C.) |
|---|---|---|---|
| | | 3.1~3.9 (4H, m), 4.58~4.64 (H, d) 7.16 (H, d), 7.80 (H, d) | |

*1 According to KBr tablet method
*2 Solvent: CDCl$_3$, Internal reference:tetramethylsilane
*3 Solvent: acetone-d$_6$, Internal reference:tetramethylsilane Referential Example 1

The 4-ethoxy-5,8-dimethylthiochroman-6-carboxylic acid-1,1-dioxide, used as a starting material in Preparation Example 1, was produced as follows.

A 100 ml three-necked flask was charged with 5.9 g (0.022 mol) of 6-bromo-5,8-dimethylthiochroman-4-one, and then, 30 ml of methylene chloride and 10 ml of methanol were added and dissolved. The entire reaction system was cooled to 0° C. in an ice salt bath, and 0.42 g.(0.011 mol) of sodium borohydride was added by small portions. Thereafter, the mixture was allowed to react for 2 hours while it was cooled as above. The reaction mixture was poured into 100 ml of water, and the mixture was extracted with methylene chloride. The extract was dried over anhydrous sodium sulfate, and methylene chloride was distilled off under reduced pressure to give 6.0 g of 6-bromo-5,8-dimethyl-4-hydroxythiochroman as a solid. Then, 6.0 g of this 6-bromo-5,8-dimethyl-4-hydroxythiochroman was charged into a 100 ml eggplant-shaped flask, and 20 ml of ethanol was added to form a solution. Then, 10 drops of concentrated sulfuric acid was added, and the mixture was refluxed under heat for 1 hour. The reaction mixture was allowed to cool and poured into 100 ml of water, and the mixture was extracted with methylene chloride. The extract was dried over anhydrous sodium sulfate, and methylene chloride was distilled off under reduced pressure to give 5.8 g of 6-bromo-5,8 -dimethyl-4-ethoxythiochroman as an oily substance.

A 200 ml three-necked flask was charged with 5.8 g of the above 6-bromo-5,8-dimethyl-4-ethoxythiochroman, and 50 ml of dry tetrahydrofuran was added to form a solution. Then, 1.7 g (0.070 mol ) of magnesium and 4.4 g (0.040 mol) of ethyl bromide were added, and the mixture was refluxed under heat for 1.5 hours. After the reaction mixture was allowed to cool, carbon dioxide gas was bubbled for 30 minutes.

Then, the entire system was cooled to 0° C. in an ice salt bath, and 50 ml of 10% hydrochloric acid was added to decompose unreacted magnesium. Ether was added to the reaction mixture, and the entirety of the mixture was taken out. The water layer was removed. Further, the organic layer was extracted with a 3% potassium carbonate aqueous solution, and then 10% hydrochloric acid was added to the extract until the mixture had pH=1, to form a solid. The formed solid was collected by filtration, whereby 4.2 g (0.016 mol) of 4-ethoxy-5,8-dimethylthiochroman-6-carboxylic acid was obtained. The yield thereof based on 6-bromo-5,8 -dimethylthiochroman-4-one was 73%.

Then, a 100 ml eggplant-shaped flask was charged with 2.4 (9.0 mmol) g of the above-obtained 4-ethoxy-5,8 -dimethylthiochroman-6-carboxylic acid, and 10 ml of acetic acid was added to form a solution. Further, 3.0 g (26 mmol) of 30% aqueous hydrogen peroxide was added, and the mixture was heated at 80° C. for 5 hours. Ethyl acetate was added to the reaction mixture, and the entirety of the resultant mixture was taken out, washed with water and dried over anhydrous sodium sulfate, and the solvent was distilled off under reduced pressure to give 2.4 g (8.1 mmol) of 4-ethoxy-5,8-dimethylthiochroman-6-carboxylic acid-1,1-dioxide as a solid (yield 89%). Table (D) shows the structural formula, infrared absorption spectrum and proton nuclear magnetic resonance spectrum data of the so-obtained compound.

Referential Example 2

The starting material used in Preparation Examples 2 and 14 was obtained in the same manner as in Referential Example 1 except that the 6-bromo-5,8-dimethylthiochroman- 4-one was replaced with 6-bromo-5-methylthiochroman-4-one, Table D shows the structural formula and nuclear magnetic resonance spectrum data of the so-obtained starting material.

Referential Example 3–5

The starting materials used in Preparation Examples 3 to 5 and 13 were obtained in the same manner as in Referential Example 2 except that the ethanol used in the etherification reaction in Referential Example 2 was replaced with n-propanol (Referential Example 3), methanol (Referential Example 4) and i-propanol (Referential Example 5).

Table D shows the structural formulae and nuclear magnetic resonance spectrum data of the so-obtained starting materials.

Referential Examples 6 and 7

The starting materials used in Preparation Examples 6, 7, 11 and 12 were obtained in the same manner as in Referential Example 1 except that the ethanol used in the etherification reaction in Referential Example 1 was replaced with methanol (Referential Example 6) and i-propanol (Referential Example 7).

Table D shows the structural formulae, IR spectra and nuclear magnetic resonance spectrum data of the so-obtained starting materials.

Referential Example 8

2.9 Grams (0.011 mol) of 4-ethoxy-5,8 -dimethylthiochroman-6-carboxylic acid was synthesized in the same manner as in Referential Example 1, and 10 ml of acetic acid and 1.3 g (0.011 mol) of a 30% aqueous hydrogen peroxide were added. The mixture was allowed to react at room temperature for 12 hours, and then the reaction mixture was poured into 100 ml of water to form a precipitated oil. The precipitated oil was extracted with ethyl acetate, dried over anhydrous sodium sulfate and concentrated under reduced pressure to give 2.5 g of the starling material used in Preparation Example 8. Table D shows the structural formula and analytical data of this starting material.

TABLE (D)

| Referential Ex. No. | Structural formula | Infrared absorption spectrum[*1] (cm$^{-1}$) | Proton nuclear magnetic resonance spectrum (ppm) |
|---|---|---|---|
| 1 | [Structure: benzene ring with CH$_3$, OC$_2$H$_5$, HO$_2$C, CH$_3$, SO$_2$ substituents] | 1730 (C=O) 2900, 2950, 3000 (C—H) 2500~3500 (O—H) | 1.26(3H, t),[*2] 2.3~2.9(2H, m) 2.54(3H, s) 2.74(3H, s) 3.1~4.0(2H, m) 3.54~3.88(2H, m) 4.62~4.68(H, m) 7.69(H, s) |
| 2 | [Structure: benzene ring with CH$_3$, OC$_2$H$_5$, HO$_2$C, SO$_2$ substituents] | — | 1.20(3H, t)[*3] 2.3~3.1(2H, m) 2.61(3H, s) 3.2~3.7(2H, m) 3.66~3.90(2H, m) 4.77~4.84(H, m) 7.77(H, d), 7.98(H, d) 9.5(H, s –) |
| 3 | [Structure: benzene ring with CH$_3$, OCH$_2$CH$_2$CH$_3$, HO$_2$C, SO$_2$ substituents] | — | 0.92(3H, t)[*3] 1.61(2H, m) 2.3~3.1(2H, m) 2.61(3H, s) 3.2~3.9(2H, m) 3.60~3.81(2H, m) 4.78~4.85(H, m) 7.78(H, d) 7.98(H, d) 9.4(H, s –) |
| 4 | [Structure: benzene ring with CH$_3$, OCH$_3$, HO$_2$C, SO$_2$ substituents] | — | 2.3~3.1(2H, m)[*3] 2.60(3H, s) 3.1~3.9(2H, m) 4.69~4.76(H, m) 7.76(H, d) 7.97(H, d) 9.1(H, s –) |
| 5 | [Structure: benzene ring with CH$_3$, OCH(CH$_3$)$_2$, HO$_2$C, SO$_2$ substituents] | 1730(C=O) 2940, 2980(C—H) 2550~3450(O—H) 1120, 1305(SO$_2$) | 1.25(6H, dd),[*3] 2.25~2.50(H, m) 2.65(3H, s), 2.80~3.10(H, m) 3.20~3.50(H, m) 3.55~3.75(H, m) 3.85~4.20(H, m) 5.00~5.10(H, m) 7.75(H, d), 7.95(H, d) |
| 6 | [Structure: benzene ring with CH$_3$, OCH$_3$, HO$_2$C, CH$_3$, SO$_2$ substituents] | 1730(C=O) 2960, 3000(C—H) 2550~3450(O—H) 1110, 1280(SO$_2$) | 2.45~2.95(2H, m)[*2] 2.53(3H, s) 2.73(3H, s) 3.20~3.35(H, m) 3.46(3H, s) 3.63~3.86(H, m) 4.50~4.60(H, m) 7.70(H, s) |
| 7 | [Structure: benzene ring with CH$_3$, OCH(CH$_3$)$_2$, HO$_2$C, CH$_3$, SO$_2$ substituents] | 1730(C=O) 2960, 2990(C—H) 2600~3500(O—H) 1120, 1290(SO$_2$) | 1.28(6H, dd),[*2] 2.30~2.90(2H, m) 2.64(3H, s), 2.77(3H, s) 3.13~3.50(H, m) 3.84(H, m) 3.68~4.08(H, m) 4.87~4.93(H, m) 7.78(H, s) |
| 8 | [Structure: benzene ring with CH$_3$, OC$_2$H$_5$, HO$_2$C, CH$_3$, SO substituents] | 1725(C=O) 2940, 2980(C—H) 2550~3450(O—H) 980(SO) | 1.24(3H, t)[*2] 2.30~2.95(2H, m) 2.53(3H, s) 2.70(3H, s) 3.05~3.50(2H, m) 3.66(2H, q) 4.58~4.73(H, m) 7.67(H, s) |

[*1] According to KBr tablet method

TABLE (D)-continued

| Referential Ex. No. | Structural formula | Infrared absorption spectrum*[1] (cm$^{-1}$) | Proton nuclear magnetic resonance spectrum (ppm) |
|---|---|---|---|

*[2]Solvent: CDCl$_3$, Internal reference: tetramethylsilane
*[3]Solvent: acetone-d$_6$, Internal reference: tetramethylsilane

HERBICIDE EXAMPLE 1

(1) Preparation of herbicide

A carrier for a wettable powder was prepared by uniformly pulverizing and mixing 97 parts by weight of talc (trade name: Zeaklite) as a carrier, 1.5 parts by weight of alkylarylsulfonic acid salt (trade name: Neoplex, supplied by Eao-Atlas K.K.) and 1.5 parts by weight of a nonionic and anionic surfactant (trade name: Sorpol 800A, supplied by Toho Chemical Co., Ltd.).

90 Parts by weight of the above carrier for a wettable powder and 10 parts by weight of one of the compounds of the present invention obtained in the above Preparation Examples were uniformly pulverized and mixed to obtain a herbicide. For comparison, 90 parts by weight of the above carrier for a wettable powder and 10 parts by weight of one of the compounds (i) to (v) to be described later were uniformly pulverized and mixed to obtain a herbicide.

(2) Test on foliar treatment 1

Seeds of weeds such as barnyardgrass, green foxtail, cocklebur, velvetleaf and slender amaranth, and seeds of corn, wheat and barley were sown in 1/5,000 are Wagner pots filled with upland soil, and covered with upland soil. Then, the seeds were grown in a greenhouse, and when they grew to plants at one or two-leaved stage, a predetermined amount of the predetermined herbicide obtained in the above (1) was suspended in water and uniformly sprayed to foliar portions at a rate of 200 liter/10 are. Thereafter the plants were grown in the greenhouse, and 20 days after the treatment, the herbicide was determined for herbicidal efficacy and phytotoxicity to the crops. Table (E) shows the results.

The compound (i) used for comparison is described in JP-B-1-30818, and has the following structural formula.

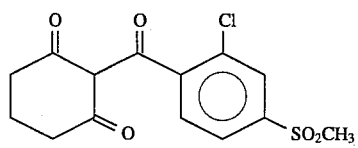

(i)

The herbicidal efficacy and the phytotoxicity to the crops are shown on the basis of the following ratings.

| (Ratings) | |
|---|---|
| | Remaining plant weight/ non-treatment ratio [%] |
| Herbicidal efficacy | |
| 0 | 81–100 |
| 1 | 61–80 |
| 2 | 41–60 |
| 3 | 21–40 |
| 4 | 1–20 |
| 5 | 0 |

-continued

| (Ratings) | |
|---|---|
| | Remaining plant weight/ non-treatment ratio [%] |
| Phytotoxicity | |
| − | 100 |
| ± | 95–99 |
| + | 90–94 |
| ++ | 80–89 |
| +++ | 0–79 |

The remaining plant weight/non-treated ratio was calculated by (remaining plant weight in treated area/remaining plant weight in non-treated area)×100.

(3) Test on upland soil treatment

Seeds of weeds such as barnyardgrass, green foxtail, cocklebur, velvetleaf and slender amaranth, and seeds of corn, wheat and barley were sown in 1/5,000 are Wagner pots filled with upland soil, and covered with upland soil. Then, a predetermined amount of the predetermined herbicide obtained in the above (1) was suspended in water and uniformly sprayed onto the soil surface. Thereafter the seeds were grown in the greenhouse, and 20 days after the treatment, the herbicide was determined for herbicidal efficacy and phytotoxicity to the crops. Table (F) shows the results.

The above herbicidal efficacy and phytotoxicity were evaluated on the same standards as those described in the above (2) Test on foliar treatment 1, and the compound (i) was used for comparison.

(4) Test on foliar treatment 2

Seeds of the following weeds and seeds of corn, wheat and barley were sown in 1/5,000 are Wagner pots filled with upland soil, and covered with upland soil. Then, the seeds were grown in a greenhouse, and when they grew to plants at one or two-leaved stage, a predetermined amount of the predetermined herbicide obtained in the above (1) was suspended in water and uniformly sprayed to foliar portions at a rate of 200 liter/10 are. Thereafter the plants were grown in the-greenhouse, and 20 days after the treatment, the herbicide was determined for herbicidal efficacy and phytotoxicity to the crops. Table (G) shows the results.

| (Tested seeds of weeds) | |
|---|---|
| Weeds | Abbreviations |
| (Gramineous weeds) | |
| Crabgrass | DA |
| Barnyardgrass | EC |
| Green foxtail | SV |
| (Broad-leaved weeds) | |
| Cocklebur | XS |

-continued

| (Tested seeds of weeds) | |
|---|---|
| Weeds | Abbreviations |
| Velvetleaf | AT |
| Pale smartweed | PL |
| Jimson weed | DS |
| Slender amaranth | AR |
| Black nightshade | SN |

The above herbicidal efficacy and phytotoxicity were evaluated on the same standards as those described in the above (2) Test on foliar treatment 1.

For comparison, the compound (ii) described in JP-A-61-155847 and the compounds (iii), (iv) and (v) described in JP-A-64-6256 were used. These compounds (ii) to (v) have the following structural formulae.

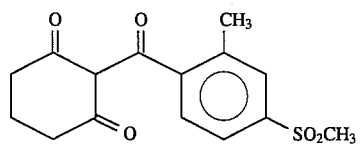
(ii)

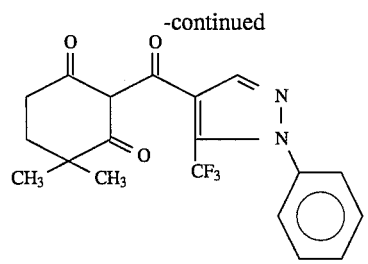
(iii)

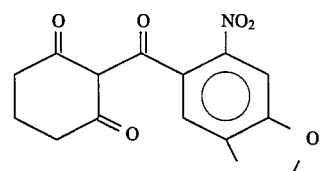
(iv)

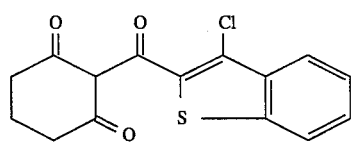
(v)

TABLE (E)

| | | | Herbicidal efficacy | | | | |
|---|---|---|---|---|---|---|---|
| Prep. Ex. No. | Test Compound | Dosage [g(a.i.)are] | Barnyard-glass | Green foxtail | Cockle-bur | Velvet leaf | Slender amaranth |
| 1 | No. 20 | 3.2 | 2 | 2 | 4 | 5 | 4 |
| 2 | No. 6 | 3.2 | 4 | 2 | 5 | 5 | 4 |
| 3 | No. 8 | 3.2 | 4 | 2 | 4 | 5 | 3 |
| 4 | No. 3 | 3.2 | 4 | 2 | 5 | 5 | 3 |
| CEx. | (i) | 3.2 | 0 | 0 | 4 | 4 | 2 |

| Prep. Ex. No. | Test Compound | Dosage [g(a.i.)a] | Phytotoxicity | | |
|---|---|---|---|---|---|
| | | | Corn | Wheat | Barley |
| 1 | No. 20 | 3.2 | — | — | — |
| 2 | No. 6 | 3.2 | — | — | — |
| 3 | No. 8 | 3.2 | — | — | — |
| 4 | No. 3 | 3.2 | — | — | — |
| CEx. | (i) | 3.2 | — | — | — | a.i. = abbreviation for active ingredient
Prep. Ex. = Preparation Example
CEx. = Comparative Example

TABLE (F)

| | | | Herbicidal efficacy | | | | |
|---|---|---|---|---|---|---|---|
| Prep. Ex. No. | Test Compound | Dosage [g(a.i.)are] | Barnyard-glass | Green foxtail | Cockle-bur | Velvet leaf | Slender amaranth |
| 1 | No. 20 | 12.5 | 4 | 5 | 5 | 5 | 5 |
| 2 | No. 6 | 12.5 | 5 | 5 | 5 | 5 | 5 |
| 3 | No. 8 | 12.5 | 4 | 4 | 5 | 5 | 4 |
| 4 | No. 3 | 12.5 | 3 | 3 | 5 | 5 | 5 |
| CEx. | (i) | 12.5 | 1 | 0 | 5 | 5 | 2 |

TABLE (F)-continued

| Prep. Ex. No. | Test Compound | Dosage [g(a.i.)a] | Phytotoxicity | | |
|---|---|---|---|---|---|
| | | | Corn | Wheat | Barley |
| 1 | No. 20 | 12.5 | — | — | — |
| 2 | No. 6 | 12.5 | — | — | — |
| 3 | No. 8 | 12.5 | — | — | — |
| 4 | No. 3 | 12.5 | — | — | — |
| CEx. | (i) | 12.5 | — | — | — | a.i. = abbreviation for active ingredient
Prep. Ex. = Preparation Example
CEx. = Comparative Example

TABLE (G)

| Prep. Ex. No. | Dosage g(a.i.)/a | Herbicidal efficacy | | | | | | | | | Phytotoxicity | | |
|---|---|---|---|---|---|---|---|---|---|---|---|---|---|
| | | DA | EC | SV | XS | AT | PL | DS | AR | SN | Corn | Wheat | Barley |
| 1 | 3.0 | 5 | 2 | 2 | 5 | 5 | 5 | 5 | 5 | 5 | — | — | — |
| 5 | 3.0 | 5 | 4 | 2 | 5 | 5 | 5 | 5 | 3 | 5 | — | — | — |
| 6 | 3.0 | 5 | 5 | 3 | 5 | 5 | 5 | 5 | 5 | 5 | — | — | — |
| 7 | 3.0 | 5 | 4 | 3 | 5 | 5 | 5 | 5 | 5 | 5 | — | — | — |
| 8 | 3.0 | 2 | 2 | 2 | 5 | 5 | 4 | 5 | 3 | 5 | — | — | — |
| 9 | 3.0 | 3 | 4 | 3 | 3 | 5 | 5 | 5 | 5 | 5 | — | — | — |
| 10 | 3.0 | 5 | 5 | 5 | 5 | 5 | 5 | 5 | 3 | 5 | — | — | — |
| 11 | 3.0 | 5 | 5 | 3 | 5 | 5 | 5 | 5 | 3 | 5 | — | — | — |
| 12 | 3.0 | 2 | 4 | 2 | 5 | 4 | 5 | 5 | 3 | 5 | — | — | — |
| 13 | 3.0 | 5 | 4 | 3 | 5 | 3 | 5 | 5 | 3 | 5 | — | — | — |
| 14 | 3.0 | 5 | 4 | 3 | 5 | 3 | 5 | 5 | 3 | 5 | — | — | — |
| 比比比 | | | | | | | | | | | | | |
| (ii) | 3.0 | 3 | 0 | 0 | 4 | 4 | 4 | 4 | 1 | 3 | — | — | — |
| (iii) | 3.0 | 2 | 1 | 0 | 3 | 2 | 2 | 4 | 1 | 3 | — | — | — |
| (iv) | 3.0 | 1 | 0 | 1 | 3 | 3 | 4 | 4 | 2 | 3 | — | — | — |
| (V) | 3.0 | 0 | 0 | 0 | 2 | 4 | 1 | 2 | — | — | — | — | — | a.i. = abbreviation of active ingredient

Tables (E), (F) and (G) clearly show that the herbicide containing the cyclohexanedione derivative, provided by the present invention, has no phytotoxicity to corn, wheat and barley and exhibits excellent herbicidal effects on gramineous weeds such as crabgrass, barnyardgrass and green foxtail and broad-leaved weeds such as cocklebur, velvetleaf, pale smartweed, Jimson weed, slender amaranth and black nightshade at low dosage. In contrast, herbicides containing the known cyclohexanedione derivatives (i), (ii), (iii), (iv) and (v) showed insufficient effects on broadleaved weeds such as cocklebur, velvetleaf, pale smartweed, slender amaranth and black nightshade, particularly they were poor in herbicidal effects on crabgrass, barnyardgrass and green foxtail.

As specified above, the present invention provides the novel cyclohexanedione derivative which exhibits high selectivity for corn, wheat and barley and can control gramineous weeds and broad-leaved weeds at a low dosage and a salt thereof; a process of the production of the above novel cyclohexanedione derivative; and a herbicide containing the above cyclohexanedione derivative and/or its salt as an active ingredient.

What is claimed is:

1. A cyclohexanedione derivative of the formula (I),

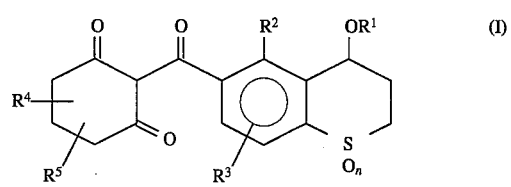

wherein $R^1$ is a $C_1$–$C_6$ alkyl group, $R^2$ is a $C_1$–$C_4$ alkyl group, each of $R^3$, $R^4$ and $R^5$ is independently hydrogen or a $C_1$–$C_4$ alkyl group, and n is an integer of 0 to 2, or a salt thereof.

2. A process for the production of the cyclohexanedione derivative of the formula (I) recited in claim 1, comprising reacting a compound of the formula (II),

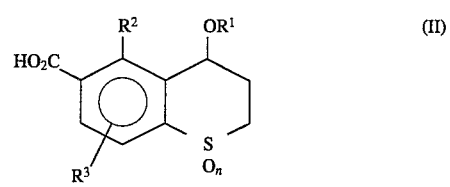

wherein $R^1$ is a $C_1$–$C_6$ alkyl group, $R^2$ is a $C_1$–$C_4$ alkyl group, $R^3$ is hydrogen or a $C_1$–$C_4$ alkyl group, and n is an integer of 0 to 2 with a halogenating agent to form a compound of the formula (III),

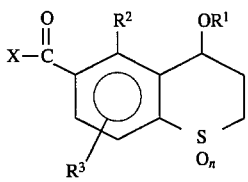

wherein $R^1$, $R^2$, $R^3$ and n are as defined above and X is a halogen atom, reacting the above compound (III) with a compound of the formula (IV),

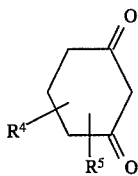

wherein each of $R^4$ and $R^5$ is independently hydrogen or a $C_1$–$C_4$ alkyl group, to form a compound of the formula (V),

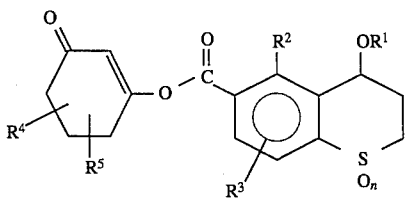

wherein $R^1$, $R^2$, $R^3$, $R^4$, $R^5$ and n are as defined above, and subjecting the above compound to a rearrangement reaction.

3. A herbicidal composition containing (i) at least one selected from the group consisting of the cyclohexanedione derivative of the formula (I) and a salt thereof, recited in claim 1 and (ii) a herbicidal carrier.

4. A cyclohexanedione derivative or a salt thereof according to claim 1, wherein $R^1$ is methyl, ethyl, propyl or butyl.

5. A cyclohexanedione derivative or a salt thereof according to claim 1, wherein $R^2$ is methyl.

6. A cyclohexanedione derivative or a salt thereof according to claim 1, wherein $R^3$ is hydrogen or methyl.

7. A cyolohexanedione derivative or a salt thereof according to claim 1, wherein $R^4$ is hydrogen or methyl.

8. A cyclohexanedione derivative or a salt thereof according to claim 1, wherein $R^5$ is hydrogen or methyl.

9. A cyclohexanedione derivative or a salt thereof according to claim 1, wherein $R^3$ is substituted on the 8-position of a thiochroman ring.

10. A cyclohexanedione derivative or a salt thereof according to claim 1, wherein $R^4$ and $R^5$ are substituted on the same carbon atom of a cyclohexan-1,3-dione ring.

11. A cyclohexanedione derivative or a salt thereof according to claim 1, wherein $R^4$ and $R^5$ are substituted on the 4-position of a cyclohexan-1,3-dione ring.

12. A cyclohexanedione derivative or a salt thereof according to claim 1, wherein n is 2.

13. A cyclohexanedione derivative or a salt thereof according to claim 1, wherein $R^1$ is methyl, ethyl, propyl or butyl;

$R^2$ is methyl;

$R^3$ is hydrogen or methyl;

$R^4$ is hydrogen or methyl;

$R^5$ is hydrogen or methyl;

$R^6$ is substituted on the 8-position of a thiochroman ring;

$R^4$ and $R^5$ are substituted on the same carbon atom at the 4-position of cyclohexan-1,3-dione ring; and n is 2.

14. A cyclohexane dione derivative according to claim 1, which is 4-ethoxy-5,8-dimethyl-6-(1,3-dioxocyclohexan-2-yl)carbonylthiochroman-1,1-dioxide.

15. A cyclohexane dione derivative according to claim 1, which is 4-ethoxy-5-methyl-6-(1,3-dioxocyclohexan-2-yl)carbonylthiochroman-1,1-dioxide.

16. A cyclohexane dione derivative according to claim 1, which is 4-n-propyloxy-5-methyl-6-(1,3-dioxocyclohexan-2yl)carbonylthiochroman-1,1-dioxide.

17. A cyclohexane dione derivative according to claim 1, which is 4-methoxy-5-methyl-6-(1,3-dioxocyclohexan-2-yl)carbonylthiochroman-1,1-dioxide.

18. A cyclohexane dione derivative according to claim 1, which is 4-i-propyloxy-5-methyl-6-(1,3-dioxocyclohexan-2-yl)carbonylthiochroman-1,1-dioxide.

19. A cyclohexane dione derivative according to claim 1, which is 4-methoxy-5,8-dimethyl-6-(1,3-dioxocyclohexan-2-yl)carbonylthiochroman-1,1-dioxide.

20. A cyclohexane dione derivative according to claim 1, which is 4-i-propyloxy-5,8-dimethyl-6-(1,3-dioxocyclohexan-2 -yl)carbonylthiochroman-1,1-dioxide.

21. A cyclohexane dione derivative according to claim 1, which is 4-ethoxy-5,8-dimethyl-6-(1,3-dioxocyclohexan-2 -yl)carbonylthiochroman-1-oxide.

22. A cyclohexane dione derivative according to claim 1, which is 4-ethoxy-5,8-dimethyl-6-(5,5-dimethyl-1,3 -dioxocyclohexan-2-yl)carbonylthiochroman-1,1-dioxide.

23. A cyclohexane dione derivative according to claim 1, which is 4-ethoxy-5,8-dimethyl-6-(4,4-dimethyl-1,3 -dioxocyclohexan-2-yl)carbonylthiochroman-1,1-dioxide.

24. A cyclohexane dione derivative according to claim 1, which is 4-methoxy-5,8-dimethyl-6-(4,4-dimethyl-1,3 -dioxocyclohexan-2-yl)carbonylthiochroman-1,1-dioxide.

25. A cyclohexane dione derivative according to claim 1, which is 4-i-propyloxy-5,8-dimethyl-6-(4,4-dimethyl-1,3 -dioxocyclohexan-2-yl)carbonylthiochroman-1,1-dioxide.

26. A cyclohexane dione derivative according to claim 1, which is 4-methoxy-5-methyl-6-(4,4-dimethyl-1,3-dioxocyclohexan- 2-yl)carbonylthiochroman-1,1-dioxide.

27. A cyclohexane dione derivative according to claim 1, which is 4-ethoxy-5-methyl-6-(4,4-dimethyl-1,3-dioxocyclohexan-2 -yl)carbonylthiochroman-1,1-dioxide.

* * * * *